United States Patent
Freeman et al.

(10) Patent No.: US 6,455,648 B1
(45) Date of Patent: Sep. 24, 2002

(54) OLEFIN PRODUCTION

(75) Inventors: Jeffrey W. Freeman, Bartlesville, OK (US); Warren M. Ewert, Bartlesville, OK (US); Bruce E. Kreischer, Bartlesville, OK (US); Ronald D. Knudsen, Bartlesville, OK (US); Glyndal D. Cowan, Bartlesville, OK (US)

(73) Assignee: Chevron Phillips Chemical Company LP, The Woodlands, TX (US)

( * ) Notice: Subject to any disclaimer, the term of this patent is extended or adjusted under 35 U.S.C. 154(b) by 0 days.

(21) Appl. No.: 09/474,067

(22) Filed: Dec. 29, 1999

(51) Int. Cl.$^7$ .............................. C08F 4/78; B01J 31/18
(52) U.S. Cl. .................... 526/161; 526/169; 526/124.1; 526/124.2; 526/124.9; 526/172; 502/123; 502/167
(58) Field of Search ................................. 526/161, 169, 526/124.1, 172; 502/123, 167

(56) References Cited

U.S. PATENT DOCUMENTS

| | | | |
|---|---|---|---|
| 5,198,563 A | 3/1993 | Reagen et al. ................. 556/57 |
| 5,288,823 A | 2/1994 | Reagan et al. ............... 526/124 |
| 5,331,070 A | 7/1994 | Pettijohn et al. ............. 526/105 |
| 5,331,104 A | 7/1994 | Reagen et al. ............... 585/512 |
| 5,340,785 A | 8/1994 | Reagen et al. ............... 502/109 |
| 5,376,612 A | 12/1994 | Reagen et al. ............... 502/104 |
| 5,393,719 A | 2/1995 | Pettijohn et al. ............. 502/113 |
| 5,399,539 A | 3/1995 | Reagen et al. ............... 502/107 |
| 5,470,926 A | 11/1995 | Reagen et al. ............... 526/120 |
| 5,523,507 A | 6/1996 | Reagen et al. ............... 585/513 |
| 5,532,375 A | 7/1996 | Galliani et al. ............... 546/334 |
| 5,689,028 A | 11/1997 | Lashier et al. ............... 585/512 |
| 5,856,257 A * | 1/1999 | Freeman et al. ............. 502/152 |

* cited by examiner

Primary Examiner—David W. Wu
Assistant Examiner—Caixia Lu
(74) Attorney, Agent, or Firm—Williams, Morgan & Amerson, P.C.

(57) ABSTRACT

A process is provided which comprises preparing an olefin oligomerization or trimerization catalyst system and producing olefins in the presence of the olefin oligomerization or trimerization catalyst system and a solvent, wherein said catalyst system preparation comprises the steps of first contacting a chromium source and a pyrrole-containing compound to form a chromium/pyrrole mixture; second, contacting said chromium/pyrrole mixture with a metal alkyl to form a catalyst system; and then contacting said catalyst system with an alpha-olefin, preferably ethylene.

15 Claims, No Drawings

OLEFIN PRODUCTION

BACKGROUND OF THE INVENTION

This invention relates to olefin production.

Olefins, primarily alpha-olefins, have many uses. For example, alpha-olefins, such as 1-hexene, can be used in hydroformulation (OXO processes). In addition to uses as specific chemicals, alpha-olefins also can be used in polymerization processes as either a monomer or comonomer to prepare polyolefins, or polymers. Several methods of producing olefins are known in the art. These processes include catalyzed dimerization and trimerization processes. Usually, these olefin production processes are exothermic reactions and can generate significant amounts of heat.

Furthermore, preparation of dimerization and trimerization catalyst systems are exothermic reactions and heat needs to be removed from the process. Heat removal requires additional, often expensive, equipment and heat can be detrimental to the activity, productivity and selectivity of the resultant catalyst system. Prior patents have taught in-situ catalyst system preparation, wherein the catalyst system is prepared in-situ in a trimerization reactor. For example, see U.S. Pat. No. 5,198,563 and U.S. Pat. No. 5,288,823.

SUMMARY OF THE INVENTION

Accordingly, it is an object of this invention to provide an improved olefin production processes.

It is a further object of this invention to provide improved olefin oligomerization and trimerization processes.

It is yet another object of this invention to provide an improved heat control of the catalyst system preparation process.

It is still a further object of this invention to provide a more efficient catalyst system production process.

It is another object of this invention to provide a continuous process to prepare an olefin trimerization catalyst system.

In accordance with this invention, a process is provided which comprises preparing an olefin oligomerization or trimerization catalyst system and producing olefins in the presence of the olefin oligomerization or trimerization catalyst system and a solvent, wherein said catalyst system preparation comprises the steps of first contacting a chromium source and a pyrrole-containing compound to form a chromium/pyrrole mixture; second, contacting said chromium/pyrrole mixture with a metal alkyl to form a catalyst system; and then contacting said catalyst system with an alpha-olefin, preferably ethylene.

In accordance with another embodiment of this invention, a process is provided which comprises preparing an olefin oligomerization or trimerization catalyst system and producing olefins in the presence of the olefin oligomerization or trimerization catalyst system and a solvent, wherein said catalyst system preparation comprises the steps of first contacting a metal alkyl and a pyrrole-containing compound to form a metal alkyl/pyrrole mixture; second, contacting said metal alkyl/pyrrole mixture with a chromium source to form a catalyst system; and then contacting said catalyst system with an alpha-olefin, preferably ethylene.

In accordance with yet another embodiment of this invention, a process is provided which consists essentially of preparing an olefin oligomerization or trimerization catalyst system and producing olefins in the presence of the olefin oligomerization or trimerization catalyst system and a solvent, wherein said catalyst system preparation comprises the steps of first contacting a chromium source and a pyrrole-containing compound to form a chromium/pyrrole mixture; second, contacting said chromium/pyrrole mixture with a metal alkyl to form a catalyst system; and then contacting said catalyst system with an alpha-olefin, preferably ethylene.

In accordance with still another embodiment of this invention, a process is provided which consists essentially of preparing an olefin oligomerization or trimerization catalyst system and producing olefins in the presence of the olefin oligomerization or trimerization catalyst system and a solvent, wherein said catalyst system preparation comprises the steps of first contacting a metal alkyl and a pyrrole-containing compound to form a metal alkyl/pyrrole mixture; second, contacting said metal alkyl/pyrrole mixture with a chromium source to form a catalyst system; and then contacting said catalyst system with an alpha-olefin, preferably ethylene.

DETAILED DESCRIPTION OF THE INVENTION

Catalyst Systems

Catalyst systems useful in accordance with this invention comprise a chromium source, a pyrrole-containing compound and a metal alkyl, all of which have been contacted and/or reacted in the presence of an unsaturated hydrocarbon. Optionally, these catalyst systems can be supported on an inorganic oxide support. These catalyst systems are especially useful for the oligomerization of olefins, such as, for example, ethylene to 1-hexene. As used in this disclosure, the term "oligomerization" broadly encompasses the combination of two olefins (dimerization) to form an olefinic product, combination of three olefins (trimerization) to form an olefinic product and combination of more than three olefins to form an olefinic product, but does not include polymerization of olefins. An oligomer can be defined as a compound made up of repeating units, whose properties can change with the addition or removal of one or a few repeating units. The properties of a polymer do not change markedly with such a modification.

The chromium source can be one or more organic or inorganic chromium compounds, wherein the chromium oxidation state is from 0 to 6. If the chromium oxidation state is 0, metallic chromium can be the chromium source. Generally, the chromium source can have a formula of $CrX_n$, wherein X can be the same or different and can be any organic or inorganic radical, and n is an integer from 1 to 6. Exemplary organic radicals can have from about 1 to about 20 carbon atoms per radical, and are selected from the group consisting of alkyl, alkoxy, carboxy, ester, ketone, and/or amido radicals. The organic radicals can be straight-chained or branched, cyclic or acyclic, aromatic or aliphatic, can be made of mixed aliphatic, aromatic, and/or cycloaliphatic groups. Exemplary inorganic radicals include, but are not limited to halides, sulfates, and/or oxides.

Preferably, the chromium source is a chromium(II)-containing and/or a chromium(III)-containing compound which can yield a catalyst system with improved oligomerization and/or trimerization activity. Most preferably, the chromium source is a chromium(III) compound because of ease of use, availability, and enhanced catalyst system activity. Exemplary chromium(III) compounds include, but are not limited to, chromium carboxylates, chromium naphthenates, chromium halides, chromium pyrrolides, and/ or chromium dionates. Specific exemplary chromium(III) compounds include, but are not limited to, chromium(III) 2,2,6,6,-tetramethylheptanedionate [Cr(TMHD)$_3$], chromium(III) 2-ethylhexanoate also called chromium(III) tris(2-ethylhexanoate) [Cr(EH)$_3$], chromium(III) naphthenate [Cr(Np)$_3$], chromium(III) chloride, chromic bromide, chromic fluoride, chromium(III) acetylacetonate, chromium (III) acetate, chromium(III) butyrate, chromium(III) neopentanoate, chromium(III) laurate, chromium(III) stearate, chromium(III) pyrrolides and/or chromium(III) oxalate.

Specific exemplary chromium(II) compounds include, but are not limited to, chromous bromide, chromous fluoride, chromous chloride, chromium(II) bis(2-ethylhexanoate), chromium(II) acetate, chromium(II) butyrate, chromium(II) neopentanoate, chromium(II) laurate, chromium(II) stearate, chromium(II) oxalate and/or chromium(II) pyrrolides.

The pyrrole-containing compound can be any pyrrole-containing compound that will react with the chromium source to form a chromium pyrrolide complex. As used in this disclosure; the term "pyrrole-containing compound" refers to hydrogen pyrrolide, i.e., pyrrole ($C_4H_5N$), derivatives of hydrogen pyrrolide, substituted pyrrolides, as well as metal pyrrolide complexes. A "pyrrolide", as used in this disclosure, is defined as a compound comprising a 5-membered, nitrogen-containing heterocycle, such as for example, pyrrole, derivatives of pyrrole, and mixtures thereof Broadly, the pyrrole-containing compound can be pyrrole and/or any heteroleptic or homoleptic metal complex or salt, containing a pyrrolide radical, or ligand. The pyrrole-containing compound can be either affirmatively added to the olefin production reaction, or generated in-situ.

Generally, the pyrrole-containing compound will have from about 4 to about 20 carbon atoms per molecule. Exemplary pyrrolides include, but are not limited to, and are selected from the group consisting of hydrogen pyrrolide (pyrrole), lithium pyrrolide, sodium pyrrolide, potassium pyrrolide, cesium pyrrolide, and/or the salts of substituted pyrrolides, because of high reactivity and activity with the other reactants. Examples of substituted pyrrolides include, but are not limited to, pyrrole-2-carboxylic acid, 2-acetylpyrrole, pyrrole-2-carboxaldehyde, tetrahydroindole, 2,5-dimethylpyrrole, 2,4-dimethyl-3-ethylpyrrole, 3-acetyl-2,4-dimethylpyrrole, ethyl-2,4-dimethyl-5-(ethoxycarbonyl)-3-pyrrole-propionate, ethyl-3,5-dimethyl-2-pyrrolecarboxylate, and mixtures thereof When the pyrrole-containing compound contains chromium, the resultant chromium compound can be called a chromium pyrrolide.

The most preferred pyrrole-containing compounds used in preparation of a trimerization catalyst system are selected from the group consisting of hydrogen pyrrolide, i.e., pyrrole ($C_4H_5N$), 2,5-dimethylpyrrole (2,5-DMP) and/or chromium pyrrolides because of enhanced olefin production activity, selectivity and/or purity. Optionally, for ease of use, a chromium pyrrolide can provide both the chromium source and the pyrrole-containing compound. As used in this disclosure, when a chromium pyrrolide is used to form a catalyst system, a chromium pyrrolide can be considered to provide both the chromium source and the pyrrole-containing compound. While all pyrrole-containing compounds can produce catalyst systems with high activity and productivity, use of pyrrole and/or 2,5-dimethylpyrrole can produce a catalyst system with enhanced activity and selectivity to a desired product.

The metal alkyl can be any heteroleptic or homoleptic metal alkyl compound. One or more metal alkyls can be used. The alkyl ligand(s) of the metal alkyl can be any aliphatic and/or aromatic radical. Preferably, the alkyl ligand (s) are any saturated or unsaturated aliphatic radical. The metal alkyl can have any number of carbon atoms per molecule. However, due to commercial availability and ease of use, the metal alkyl usually will comprise less than about 70 carbon atoms per metal alkyl molecule and preferably less than about 20 carbon atoms per molecule. Exemplary metal alkyl compounds include, but are not limited to, alkylaluminum compounds, alkylboron compounds, alkylmagnesium compounds, alkylzinc compounds and/or allyl lithium compounds. Exemplary metal alkyls include, but are not limited to, n-butyl lithium, sec-butyllithium, tert-butyllithium, diethylmagnesium, diethylzinc, triethylaluminum, trimethylaluminum, triisobutylalumium, and mixtures thereof.

Preferably, the metal alkyl is selected from the group consisting of non-hydrolyzed, i.e., not pre-contacted with water, alkylaluminum compounds, derivatives of alkylaluminum compounds, halogenated alkylaluminum compounds, and mixtures thereof for improved product selectivity, as well as improved catalyst system reactivity, activity, and/or productivity. The use of hydrolyzed metal alkyls can result is decreased olefin, i.e., liquid, production and increased polymer, i.e., solid, production.

Most preferably, the metal alkyl is a non-hydrolyzed alkylaluminum compound, expressed by the general formulae $AlR_3$, $AlR_2X$, $AlRX_2$, $AlR_2OR$, $AlRXOR$, and/or $Al_2R_3X_3$, wherein R is an alkyl group and X is a halogen atom. Exemplary compounds include, but are not limited to, triethylaluminum, tripropylaluminum, tributylaluminum, diethylaluminum chloride, diethylaluminum bromide, diethylaluminum ethoxide, diethylaluminum phenoxide, ethylaluminum dichloride, ethylaluminum sesquichloride, and mixtures thereof for best catalyst system activity and product selectivity. The most preferred alkylaluminum compounds are triethylaluminum (TEA) and diethylaluminum chloride (DEAC); TEA is used for best results in catalyst system activity and product selectivity and DEAC is used for best results in catalyst product purity and selectivity.

While not wishing to be bound by theory, it is believed that a chloride containing-compound can improve product purity and selectivity. Any chloride-containing compound can be used, such as, for example, DEAC and organo chlorides. Exemplary organochlorides include, but are not limited to, carbon tetrachloride,methylene chloride, chloroform, benzylchloride, 1-hexachloroethane and mixtures thereof.

Usually, contacting and/or reacting of the chromium source, pyrrole-containing compound and metal alkyl is done in the presence of an unsaturated hydrocarbon. The unsaturated hydrocarbon can be any aromatic or aliphatic hydrocarbon, in a gas, liquid or solid state. Preferably, to affect thorough contacting of the chromium source, pyrrole-containing compound, and metal alkyl, the unsaturated hydrocarbon will be in a liquid state. The unsaturated hydrocarbon can have any number of carbon atoms per molecule. Usually, the unsaturated hydrocarbon will comprise less than about 70 carbon atoms per molecule, and preferably, less than about 20 carbon atoms per molecule, due to commercial availability and ease of use. Exemplary unsaturated, aliphatic hydrocarbon compounds include, but are not limited to, ethylene, 1-hexene, 1,3-butadiene, and mixtures thereof The most preferred unsaturated aliphatic hydrocarbon compound is 1-hexene, because of elimination of catalyst system preparation steps and 1-hexene can be a reaction product. Exemplary aromatic hydrocarbons include, but are not limited to, benzene, toluene, ethylbenzene, xylene, mesitylene, hexamethylbenzene, and mixtures thereof. Unsaturated, aromatic hydrocarbons are preferred in order to improve catalyst system stability, as well as produce a highly active and selective catalyst system. The preferred unsaturated aromatic hydrocarbon is selected from the group consisting of toluene, ethylbenzene, and mixtures thereof The most preferred aromatic hydrocarbon is ethylbenzene for best catalyst system activity, productivity and product selectivity.

It should be recognized, however, that the reaction mixture comprising a chromium source, pyrrole-containing compound, metal alkyl and unsaturated hydrocarbon can contain additional components which do not adversely affect and can enhance the resultant catalyst system, such as, for example, transitions metals and/or halides.

The order of combination of the catalyst system component during catalyst system preparation in accordance with this invention is critical. At all times, catalyst system components must be combined in the orders disclosed and claimed in this invention prior to contacting ethylene. In accordance with one embodiment of the invention, the first step of catalyst system preparation must be to combine the metal alkyl and the pyrrole-containing compound. These two components can be combined in accordance with any method known in the art and preferably in the presence of an unsaturated hydrocarbon, as disclosed. Such a combination forms a metal alkyl/pyrrole solution.

The amounts of each component used to form the metal alkyl/pyrrole solution can be any amount sufficient to form an active catalyst system when combined with a chromium-containing compound. Generally, a molar excess of the metal alkyl is used. Expressed as a molar ratio, in terms of moles of nitrogen (N) in the pyrrole compound to moles of metal (M) in the metal alkyl, usually at least a one-hundred-fold molar excess of metal is used. As used in this disclosure, the metal (M) is aluminum. Preferably, the N:M molar ratio is within a range of about 3:3 to about 3:50. Most preferably, the N:M molar ratio is within a range of 1:3 to 1:7. Too much metal alkyl does not provide any significant economic improvement to catalyst system activity and too little metal alkyl can result in catalyst system with poor performance, i.e., insufficient activity and productivity.

Contacting of the metal alkyl and pyrrole-containing compound can be done under any conditions sufficient to thoroughly contact the two components, however, all contacting must be done in an inert atmosphere, such as, for example, nitrogen and/or argon. For ease of preparation, contacting usually is done under conditions of ambient temperature and pressure. Contact time can range from seconds to hours, preferably 1 second to 4 hours. Longer contacting times do not provide any additional catalyst system benefit.

The second step for catalyst system preparation in accordance with this embodiment of the invention is to incrementally, or slowly, add the chromium-containing compound to the metal alkyl/pyrrole solution. The manner of addition of the chromium-containing compound to the metal alkyl/pyrrole solution is critical in that the chromium must be added slowly or incrementally. Such incremental addition of the chromium-containing compound to the solution provides better heat control of the catalyst system during catalyst system preparation. while not wishing to be bound by theory, it is believed that excess heat during catalyst system preparation can result in a less active catalyst system.

The amounts of each component, chromium-containing compound and metal alkyl/pyrrole solution, used to form the final catalyst system can be any amount sufficient to form an active catalyst system. Generally, the amount of metal alkyl/pyrrole solution used is determined based on the moles of chromium. Expressed as a molar ratio, in terms of moles of chromium (Cr) to moles of nitrogen (N) in the pyrrole compound to moles of metal (M) in the metal alkyl, usually at least a fifteen-fold molar excess of pyrrole-containing compound and a one hundred fifty-fold molar excess of metal alkyl is used over the amount of chromium used. Preferably, the Cr:N:M molar ratio is within a range of about 3:3:3 (also expressed as about 1:1:1) to about 1:3:100. Most preferably, the Cr:N:M molar ratio is within a range of 1:3:9 to 1:3:21. Too much of any of the catalyst system components does not provide any significant economic improvement to catalyst system activity and too little of any of the catalyst system components can result in catalyst system with poor performance, i.e., insufficient activity and productivity. It has been found that an increase in the amount of metal (aluminum) in the reactor can allow a decrease in the amount of chromium in the reactor. However, an increase of aluminum and decrease of chromium in the reactor can result in increased productivity, but decreased purity and increased polymer production.

As stated earlier, the catalyst synthesis prepared in a hydrocarbon solvent, also called a catalyst system solution. The resultant catalyst system, prior to introduction to any of the reactant, usually has a chromium concentration of about less than about 50 mg Cr/ml catalyst system solution, preferably within a range of about 0.01 mg Cr/mL catalyst system solution to about 25 mg Cr/ml catalyst system solution. Most preferably, the chromium concentration in the catalyst system solution is within a range of 1 mg Cr/ml catalyst system solution to 10 mg Cr/ml catalyst system solution for best catalyst system activity, selectivity and productivity.

The metal alkyl/pyrrole solution and the chromium-containing compound solution must be combined prior to contacting any reactants. Any method of contacting known in the art can be used. For example, contacting of these two catalyst system components can be done in a batch process and stored for later use in a trimerization reactor or the two components can be continuously contacted and fed as one stream into an oligomerization or trimerization reactor.

Contacting of the metal alkyl/pyrrole solution and the chromium solution can be done under any conditions sufficient to form an active trimerization catalyst system. All contacting must be done under an inert atmosphere, such as, for example, nitrogen and/or argon. Contacting conditions can be any conditions sufficient to form an active trimerization catalyst. Generally, conditions of ambient temperature and pressure are used. Contact time can be from less than a second to several hours. Preferably, contact time is about 1 second to 4 hours. Contact times of greater than 4 hours do not result in any additional catalyst system enhancement.

In a second embodiment of the invention, the first step of catalyst system preparation must be to combine the chromium compound and the pyrrole-containing compound. These two components can be combined in any method known in the art and preferably in the presence of an unsaturated hydrocarbon, as disclosed. Such a combination forms a chromium/pyrrole solution.

Reactants

Trimerization, as used in this disclosure, is defined as the combination of any two, three, or more olefins, wherein the number of olefin, i.e., carbon-carbon double bonds is reduced by two. Reactants applicable for use in the trimerization process of this invention are olefinic compounds which can a) self-react, i.e., trimerize, to give useful products such as, for example, the self reaction of ethylene can give 1-hexene and the self-reaction of 1,3-butadiene can give 1,5-cyclooctadiene; and/or b) olefinic compounds which can react with other olefinic compounds, i.e., co-trimerize, to give useful products such as, for example, co-trimerization of ethylene plus hexene can give 1-decene, co-trimerization of ethylene and 1-butene can give 1-octene, co-trimerization of 1-decene and ethylene can give 1-tetradecene, 1-octadecene and/or 1-docosene. For example, the number of olefin bonds in the combination of three ethylene units is reduced by two, to one olefin bond, in 1-hexene. In another example, the number of olefin bonds in the combination of two 1,3-butadiene units, is reduced by two, to two olefin bonds in 1,5-cyclooctadiene. As used herein, the term "trimerization" is intended to include dimerization of diolefins, as well as "co-trimerization", both as defined above.

Suitable trimerizable olefin compounds are those compounds having from about 2 to about 30 carbon atoms per molecule and having at least one olefinic double bond. Exemplary mono-1-olefin compounds include, but are not limited to acyclic and cyclic olefins such as, for example, ethylene, propylene, 1-butene, isobutylene, 1-pentene, 4-methyl-1-pentene, 1-hexene, 1-heptene, the four normal octenes, the four normal nonenes, vinylcyclohexane and mixtures of any two or more thereof Exemplary monoolefins include, but are not limited to, 2-butene, 2-pentene, 2-hexene, 3-hexene, 2-heptene, 3-heptene, cyclohexene and mixtures of two or more thereof. Exemplary diolefin compounds include, but are not limited to, 1,3-butadiene, 1,4-pentadiene, and 1,5-hexadiene. If branched and/or cyclic olefins are used as reactants, while not wishing to be bound by theory, it is believed that stearic hindrance could hinder the trimerization process. Therefore, the branched and/or cyclic portion(s) of the olefin preferably should be distant from the carbon-carbon double bond.

Catalyst systems produced in accordance with this invention are particularly suitable for and preferably are employed as trimerization catalyst systems.

Reaction Conditions

The reaction products, i.e., olefin trimers as defined in this specification, can be prepared from the catalyst systems of this invention by solution, slurry, and/or gas phase reaction techniques using conventional equipment and contacting processes. Contacting of the monomer or monomers with a catalyst system can be effected by any manner known in the art. One convenient method is to suspend the catalyst system in an organic medium and to agitate the mixture to maintain the catalyst system in solution throughout the trimerization process. Other known contacting methods can also be employed.

For example, the trimerization process can be carried out in a slurry of the catalyst components in an inert medium or diluent which is the process medium. Broadly, the common diluents are fluid paraffins, cycloparaffins, or aromatic hydrocarbons. Exemplary reactor diluents include, but are not limited to, isobutane, cyclohexane, and methylcyclohexane. Isobutane can be used for enhanced compatibility with known olefin polymerization processes. However, a homogenous trimerization catalyst system is more easily dispersed in cyclohexane. Therefore, a preferred diluent for a homogeneous catalyzed trimerization process is cyclohexane.

In accordance with another embodiment of this invention, a slurry process can be carried out in a diluent (medium), which is a product of the olefin oligomerization process. Therefor, the choice of reactor diluent, or medium, is based on the selection of the initial olefin reactant. For example, if the oligomerization catalyst is used to trimerize ethylene to 1-hexene, the solvent for the oligomerization reaction would be 1-hexene. If ethylene and hexene were trimerized to produce 1-decene, the oligomerization reaction solvent would be 1-decene. If 1,3-butadiene was trimerized to 1,5-cyclooctadiene, the trimerization reactor solvent would be 1,5-cyclooctadiene.

Optionally, based on economics, a solvent different than one of the oligomerization process products can be used during startup, or initiation, of the oligomerization process. A different inert diluent, such as a paraffin, cycloparaffin, or aromatic hydrocarbon, can be used during the oligomerization process initiation. Exemplary initial reactor diluents include, but are not limited to, isobutane and cyclohexane. Once the reactor has been charged with catalyst, reactant and optional diluent, additional diluent can be added to the reactor, as needed. During the course of the oligomerization reaction, the added, inert diluent will become diluted and ultimately removed from the oligomerization process reactor. Reaction temperatures and pressures can be any temperature and pressure which can trimerize the olefin reactants.

Generally, reaction temperatures are within a range of about 0° to about 250° C. Preferably, reaction temperatures within a range of about 60° to about 200° C. and most preferably, within a range of 80° to 150° C. are employed. Too low of a reaction temperature can produce too much undesirable insoluble product, such as, for example, polymer, and too high of a temperature can cause decomposition of the catalyst system and reaction products.

Generally, reaction pressures are within a range of about atmospheric to about 2500 psig. Preferably, reaction pressures within a range of about atmospheric to about 1000 psig and most preferably, within a range of 300 to 800 psig are employed. Too low of a reaction pressure can result in low catalyst system activity.

Optionally, hydrogen can be added to the reactor to accelerate the reaction and/or increase catalyst system activity. If desired, hydrogen also can be added to the reactor to control, i.e. minimize, solids (polymer) production.

Catalyst systems of this invention are particularly suitable for use in trimerization processes.

Products

The olefinic products of this invention have established utility in a wide variety of applications, such as, for example, as monomers for use in the preparation of homopolymers, copolymers, and/or terpolymers.

Further understanding of the present invention and its advantages will be provided by reference to the following examples.

EXAMPLES

Example I

This example demonstrates regular chromium addition and flow chromium addition. Catalyst systems were prepared under an inert atmosphere (nitrogen or helium) at ambient temperatures, according to the following procedure. To a clean, nitrogen purged, 5 gallon reactor, 14.14 lbs of dry, nitrogen purged, ethylbenzene were added. Then 389 mls of 2,5-dimethylpyrrole (2,5-DMP) was added to the reactor. With mixing and cooling, an aluminum alkyl mixture comprising 1599.9 g of triethylaluminum (TEA) and 1228.7 g of diethylaluminum chloride (DEAC) is pressured by nitrogen into the same 5 gallon reactor. With coolint, the temperature increased about 11° C. The reactor was stirred and cooled by an internal cooling coil during addition of the aluminum alkyl mixture. The lines containing the alkylaluminum mixture were flushed with 0.2 lbs of ethylbenzene into the reactor. In a separate container, 630.9 grams of chromium(III)ethylhexanoate ($Cr(EH)_3$) were dissolved in 750 ml of ethylbenzene in a flask purged with nitrogen. The $Cr(EH)_3$/ethylbenzene mixture was allowed to cool. After cooling, the $CrEH_3$/ethylbenzene material was added to the reactor and a temperature rise of 14° C. was observed. The reactor was stirred and cooled by an internal cooling coil during this addition. Then, the $Cr(EH)_3$ lines were flushed with 1 pound of ethylbenzene. After about 15 minutes of mixing and cooling, the reactor was allowed to set without stirring prior to filtration and dilution with either cyclohexane or methylcyclohexane, the reaction diluent.

Slow, or incremental, addition of the chromium compound followed the procedure as described above except that the chromium solution was added in 19 or 20 50 gram increments. The temperature rise after each incremental addition was only about 1° C. The data in Table 1, Runs 101–104, provide the results of the regular chromium addition. Runs 105–108 show the results of the incremental chromium addition.

trimerization process can cause the reactor to foul more frequently and require more down time for cleaning of the reactor.

Example II

Catalyst systems in this Example were prepared by making two stock solutions. The first stock solution was prepared by dissolving 23.8 grams of $Cr(EH)_3$ in a 100 ml toluene. Then 8.8 ml of 2,5-DMP was added and the total mixture was diluted to 500 ml with toluene. The second stock solution was prepared by mixing 66.9 ml of 1.8 M ethylaluminum dichloride (EADC), in toluene, with 58.8 ml of neat TEA and diluting this stock mixture to 500 ml with toluene. 28 ml of the chromium and pyrrole stock solution combined in a first container and diluted to 50 ml with toluene; 28 ml of the aluminum alkyl stock solution was added to a second container and diluted to 50 ml with toluene. Both containers were emptied at the same rate through a mixing tee (T) into a third container where the two solutions were mixed for 5 minutes. Solvent was removed by vacuum and the residue was diluted to 25 ml with cyclohexane.

Aliquots of this catalyst system were tested in a 1 liter batch reactor at a reaction temperature of 110° C., with 450 ml cyclohexane as the solvent. Then, 50 psig hydrogen was added and ethylene was fed on demand to maintain a reactor pressure of 750 psig for 30 minutes. Four runs using the above-described catalyst system are shown below in Table 2 as Runs 201–204. Runs 205–208 provide the results in which the catalyst components were added sequentially.

TABLE 1

| Run No. | Total Polymer 1-$C_6$=, (grams) | Purity 1$C_6$=/$C_6$=, % | $C_2$= Conv, % | Productivity, gm 1-$C_6$=/gm Cr | 100 MM lbs 1-$C_6$= lbs Total polym/hr | 100 MM lbs 1-$C_6$= Lbs Rx polymer/hr | 100 MM lbs 1-$C_6$= Lbs Filter polym/hr |
|---|---|---|---|---|---|---|---|
| 101 | 0.18 | 80.2 | 98.6 | 89.1 | 42,000 | 1.40 | 0.00 | 1.40 |
| 102 | 0.08 | 86.2 | 98.9 | 84.9 | 43,000 | 0.61 | 0.00 | 0.61 |
| 103 | 0.20 | 83.2 | 98.8 | 88.7 | 44,000 | 1.50 | 0.00 | 1.50 |
| 104 | 0.46 | 84.3 | 98.9 | 86.9 | 44,000 | 3.46 | 0.00 | 3.46 |
| 105 | 0.29 | 90.6 | 99.1 | 80.0 | 43,000 | 2.17 | 0.00 | 2.17 |
| 106 | 0.21 | 86.3 | 98.9 | 84.5 | 43,000 | 1.60 | 0.00 | 1.60 |
| 107 | 0.01 | 82.8 | 98.9 | 88.3 | 43,000 | 0.06 | 0.06 | 0.00 |
| 108 | 0.11 | 85.9 | 98.9 | 87.5 | 45,000 | 0.80 | 0.14 | 0.66 |

The data in Table 1 show that the slow, or incremental, addition of the chromium solution results in a higher conversion of olefins per gram of chromium per hour, as well as increased 1-hexene selectivity and purity. Furthermore, the advantage of first combining the pyrrole and the alkylaluminum compound and then subsequently adding the chromium compound and finally introducing the ethylene into the reactor is economically advantageous because an operator can decrease the amounts of pyrrole and aluminum alkyl needed for the reaction. In addition, an advantage of this catalyst system preparation reaction order is that the amount of precipitate produced is decreased. While not wishing to be bound by theory, it is believed that the amount of precipitate produced by catalyst system production can impact the amount of polymer produced in the reactor; an increase in the amount of precipitate usually can result in an increase in the amount of polymer production. It is known that an increased amount of polymer produced during the

TABLE 2

| Run No. | g/g Cr-hr Olefins | Total Polymer (grams) | Selectivity 1-Hexene, % | Purity (1-$C_6$=/$C_6$, %) | Mixed Decenes, % |
|---|---|---|---|---|---|
| 205 | 84,800 | 0.007 | 95.0 | 99.4 | 3.89 |
| 206 | 63,100 | 0.103 | 96.2 | 99.6 | 2.89 |
| 207 | 73,400 | 0.094 | 96.4 | 99.6 | 2.62 |
| 208 | 64,100 | 0.126 | 95.6 | 99.5 | 3.24 |
| 201[a] | 67,500 | 0.036 | 95.3 | 99.4 | 3.51 |
| 202[b] | 66,400 | 0.018 | 95.1 | 99.3 | 3.65 |
| 203[b] | 70,500 | 0.010 | 95.0 | 99.3 | 3.65 |
| 204[b] | 80,500 | 0.063 | 95.1 | 99.4 | 3.58 |

[a]$Cr(EH)_3$ mixed with 750 mls ethylbenzene.
[b]$Cr(EH)_3$ mixed with 364 mls ethylbenzene.

The data in Table 2 show that even without cooling, continuous preparation of catalyst system produces good trimerization product and has good commercial potential.

Example III

The following example demonstrates continuous catalyst system preparation at low concentrations. The following solutions . . .

Continuous Catalyst Preparation at Low Concentration

The following three solutions were prepared in advance. 116 g of diethylaluminum chloride (DEAC), 151 g triethylaluminum (TEA) and 178 g ethylbenzene were added to a 1 gallon cylinder under nitrogen. 2,5-Dimethylpyrrole (16.8 g) was diluted to 250 mL with ethylbenzene and added to a 300 mL cylinder under an inert atmosphere. Chromium(III) 2-ethylhexanoate (16.6 g) was dissolved in 375 g ethylbenzene and rinsed into a 1 gallon cylinder with 44 g ethylbenzene and purged with nitrogen.

Ethylbenzene (225 mL) was added to a 1 liter autoclave reactor to provide material to reach the stirrer. The reactor was purged with dry nitrogen to avoid the presence of air or moisture. For three hours the TEA and DEAC solution was pumped simultaneously with the 2,5-dimethylpyrrole solution into the 1 liter reactor at 50 mL/hour. The temperature ranged from 9.7° C. to 21° C. The reactor pressure was 95 to 107 psig. The reactor was stirred for 15 minutes after all the reactants had been pumped into the reactor. The contents of the reactor contained a pyrrole/aluminum alkyl mixture and was pressured with nitrogen into a 1 gallon cylinder. The pyrrole/aluminum alkyl mixture was then pumped into the 1-liter reactor simultaneously with the chromium(III)2-ethylhexanoate solution for three hours at 50 mL/hr. Cooling was added to the reactor and the temperature ranged between 25.3° C. and 26.5° C. The pressure was 110–113 psig. The material was stirred for 15 minutes after all the reactants had been pumped into the reactor. This catalyst was tested and found to be active as shown in Table 3.

TABLE 3

Comparison of Continuous and Slow Addition Catalyst Preparations

| | Run No. | Total Polymer (grams) | 1-$C_6$=, % | Purity 1$C_6$=/$C_6$=, % | C2= Conv |
|---|---|---|---|---|---|
| Continuous Catalyst Preparation | 301 | 0.72 | 88.2 | 99.2 | 71.69 |
| Slow Addition Catalyst Preparation | 302 | 0.81 | 91.0 | 99.1 | 80.2 |

| Productivity | lbs Total polm/hr | lbs Rx polm/hr | lbs Filter polm/hr |
|---|---|---|---|
| 76500 | 4.63 | 0.00 | 4.63 |
| 73766 | 4.75 | 0.00 | 4.75 |

This demonstrates that continuous catalyst preparation (Run 301) is comparable to the slow addition catalyst preparation (Run 302) and may have advantages on a commercial scale.

Example IV

The following example demonstrates continuous catalyst system preparation at high concentrations. The following solutions . . .

Continuous Catalyst Preparation at High Concentration

The following three solutions were prepared in advance. 154 g of diethylaluminum chloride (DEAC), 200 g triethylaluminum (TEA) and 100 g ethylbenzene were added to a 1 gallon cylinder under nitrogen. 2,5-Dimethylpyrrole (76.9 g) was diluted to 250 mL with ethylbenzene and added to a 300 mL cylinder under an inert atmosphere. Chromium(III) 2-ethylhexanoate (130.2 g) was dissolved in 280 g ethylbenzene and rinsed into a 1 gallon cylinder with 40 g ethylbenzene and purged with nitrogen.

Ethylbenzene (225 mL) was added to a 1 liter autoclave reactor to provide material to reach the stirrer. The reactor was purged with dry nitrogen to avoid the presence of air or moisture. For three hours the TEA and DEAC solution was pumped simultaneously with the 2,5-dimethylpyrrole solution into the 1 liter reactor. The aluminum alkyls were pumped at 100 mL/hour while the pyrrole solution was pumped at the rate of 30 mL/hr. The temperature ranged from 12.5° C. to 23.5° C. The reactor pressure was 89 to 119 psig. The reactor was stirred for 15 minutes after all the reactants had been pumped into the reactor. The contents of the reactor contained a pyrrole/aluminum alkyl mixture and was pressured with nitrogen into a 1 gallon cylinder. The pyrrole/aluminum alkyl mixture was then pumped into the 1 liter reactor simultaneously with the chromium(III)2-ethylhexanoate solution for three hours. The pyrrole/aluminum alkyl mixture was pumped at 100 mL/hr and the chromium solution was pumped in at a rate of 30 mL/hr. Cooling was added to the reactor and the temperature ranged between 23.0° C. and 25.2° C. The pressure was 10614 psig. The material was stirred for 15 minutes after all the reactants had been pumped into the reactor. This catalyst was tested and found to be active and demonstrated comparable activity as in Example III.

While this invention has been described in detail for the purpose of illustration, it is not to be construed as limited thereby but is intended to cover all changes and modifications within the spirit and scope thereof That which is claimed is:

1. A process to oligomerize olefins in the presence of an olefin oligomerization catalyst system wherein said oligomerization catalyst system preparation comprises the steps of:
   a) contacting a metal alkyl and a pyrrole-containing compound in the presence of an unsaturated hydrocarbon to form a metal alkyl/pyrrole mixture;
   b) contacting said metal alkyl/pyrrole mixture with a chromium source to form a catalyst system;
   and then contacting said catalyst system with an alpha-olefin.

2. A process according to claim 1, wherein said oligomerization process is a trimerization process.

3. A process according to claim 1, wherein said chromium source is selected from the group consisting of chromium (II)-containing compounds, chromium(III)-containing compounds, and mixtures thereof.

4. A process according to claim 3, wherein said chromium source is a chromium(III)-containing compound selected from the group consisting of chromium carboxylates, chromium naphthanates, chromium halides, chromium pyrrolides, chromium dionates and mixtures of two or more thereof.

5. A process according to claim 4, wherein said chromium source is selected from the group consisting of chromium (III) 2,2,6,6-tetramethylheptanedionate[Cr(TMEHD)$_3$], chromium(III) 2-ethylhexanoate[Cr(EH)3], chromium(III) tris(2-ethylhexanoate), chromium(III) naphthanate [Cr(Np) 3)$_3$], chromium(III) chloride, chromic bromide, chromic fluoride, chromium(III) acetylacetonate, chromium(III) acetate, chromium(III) butyrate, chromium(III) neopentanoate, chromium(III) laurate, chromium(III) stearate, chromium(III) pyrrolides, chromium(III) oxalate, and mixtures of two or more thereof.

6. A process according to claim 1, wherein said metal alkyl is a non-hydrolyzed metal alkyl and is selected from the group consisting of alkyl aluminum compounds, alkyl boron compounds, alkyl magnesium compounds, alkyl zinc compounds, alkyl lithium compounds, and mixture of two or more thereof.

7. A process according to claim 6, wherein said non-hydrolyzed metal alkyl is an alkylaluminum compound.

8. A process according to claim 7, wherein said alkyl aluminum compound is triethylaluminum.

9. A process according to claim 1, wherein said pyrrole-containing compound is selected from the group consisting of pyrrole, derivatives of pyrrole, alkali metal pyrrolides, salts of alkali metal pyrrolides, and mixtures thereof.

10. A process according to claim 9, wherein said pyrrole-containing compound is selected from the group consisting of hydrogen pyrrolide, 2,5-dimethylpyrrole, and mixtures thereof.

11. A process according to claim 1, wherein said catalyst system further comprises a halide source.

12. A process according to claim 1, wherein said olefin has from about 2 to about 30 carbon atoms per molecule.

13. A process according to claim 12, wherein said olefin is ethylene.

14. A process according to claim 1, wherein said unsaturated hydrocarbon is an olefin having from about 2 to about 30 carbon atoms per molecule.

15. A process according to claim 14, wherein said unsaturated hydrocarbon is 1-hexene.

* * * * *